United States Patent
Chang et al.

(10) Patent No.: US 11,697,020 B2
(45) Date of Patent: Jul. 11, 2023

(54) METHOD FOR GENERATING STIMULATION PARAMETERS, ELECTRICAL STIMULATION CONTROL APPARATUS AND ELECTRICAL STIMULATION SYSTEM

(71) Applicant: A-Neuron Electronic Corporation, Hsinchu County (TW)

(72) Inventors: Chia-Chi Chang, Taipei (TW); Pei-Chen Lin, Hsinchu (TW); Cheng-Hsiang Cheng, New Taipei (TW); Po-Huang Chen, Hsinchu (TW)

(73) Assignee: A-Neuron Electronic Corporation, Hsinchu County (TW)

( * ) Notice: Subject to any disclaimer, the term of this patent is extended or adjusted under 35 U.S.C. 154(b) by 254 days.

(21) Appl. No.: 16/952,100

(22) Filed: Nov. 19, 2020

(65) Prior Publication Data
US 2022/0152392 A1    May 19, 2022

(51) Int. Cl.
*A61N 1/36*    (2006.01)
*A61B 5/369*    (2021.01)

(52) U.S. Cl.
CPC .......... *A61N 1/36064* (2013.01); *A61B 5/369* (2021.01); *A61N 1/36139* (2013.01)

(58) Field of Classification Search
CPC ............ A61N 1/36064; A61N 1/36139; A61N 1/36146; A61N 1/36135; A61N 1/36025; A61N 1/36031; A61N 1/36034; A61N 1/36082; A61N 1/36171; A61N 1/36178; A61B 5/369; A61B 5/4094; A61B 5/7235; A61B 5/7257; A61B 5/726; A61B 5/374

See application file for complete search history.

(56) References Cited

U.S. PATENT DOCUMENTS 6,480,743 B1    11/2002    Kirkpatrick et al.
8,805,525 B2    8/2014    Gerber et al.
(Continued)

FOREIGN PATENT DOCUMENTS

| CN | 107361765 | 11/2017 |
| CN | 110418664 | 11/2019 |

(Continued)

OTHER PUBLICATIONS

Civera, M.; Surace, C. A Comparative Analysis of Signal Decomposition Techniques for Structural Health Monitoring on an Experimental Benchmark. Sensors 2021, 21, 1825. https://doi.org/10.3390/s21051825 (Year: 2021).*

(Continued)

*Primary Examiner* — Amanda K Hulbert
*Assistant Examiner* — Natasha Patel
(74) *Attorney, Agent, or Firm* — JCIP Global Inc.

(57) ABSTRACT

A method for generating stimulation parameters, an electrical stimulation control apparatus and an electrical stimulation system are provided. After receiving a brainwave signal, the brainwave signal is decomposed to obtain a first sub-signal and a second sub-signal. Then, the first sub-signal is analyzed to obtain an intrinsic frequency series, and the second sub-signal is converted to a Boolean signal. Subsequently, the intrinsic frequency series and the Boolean signal, which serve as a set of stimulation parameters, are outputted to the stimulator, enabling the stimulator to generate a stimulus signal.

15 Claims, 2 Drawing Sheets

(56) References Cited

U.S. PATENT DOCUMENTS

| | | |
|---|---|---|
| 9,209,782 B2 | 12/2015 | Ricci et al. |
| 10,130,813 B2 | 11/2018 | Crowder et al. |
| 2003/0167019 A1 | 9/2003 | Viertio-Oja et al. |
| 2009/0048530 A1* | 2/2009 | Sarkela ............... A61B 5/4094 600/544 |
| 2016/0228705 A1* | 8/2016 | Crowder ............ A61N 1/36139 |
| 2019/0001140 A1* | 1/2019 | Tass ................... A61N 1/36167 |
| 2019/0247662 A1 | 8/2019 | Poltroak |
| 2019/0321638 A1 | 10/2019 | Mogul |
| 2020/0205739 A1* | 7/2020 | Garrett .................. G16H 50/30 |

FOREIGN PATENT DOCUMENTS

| | | | |
|---|---|---|---|
| TW | I492738 | 7/2015 | |
| TW | I562758 | 12/2016 | |
| TW | 201806370 | 2/2018 | |
| WO | 2006081125 | 8/2006 | |
| WO | 2006083626 | 8/2006 | |
| WO | WO-2009155172 A2 * | 12/2009 | ........... A61B 5/0006 |
| WO | WO-2018102815 A1 * | 6/2018 | ......... A61B 5/04001 |

OTHER PUBLICATIONS

"Office Action of Taiwan Counterpart Application", dated Jul. 7, 2021, p. 1-p. 3.

Eric H Kossoff et al., "Effect of an external responsive neurostimulator on seizures and electrographic discharges during subdural electrode monitoring." Epilepsia, vol. 45, No. 12, Dec. 2004, pp. 1560-1567.

Ivan Osorio et al., "Automated seizure abatement in humans using electrical stimulation," Ann Neurol, vol. 57, No. 2, Feb. 2005, pp. 258-268.

"Search Report of Europe Counterpart Application", dated Jun. 4, 2021, p. 1-p. 8.

* cited by examiner

METHOD FOR GENERATING STIMULATION PARAMETERS, ELECTRICAL STIMULATION CONTROL APPARATUS AND ELECTRICAL STIMULATION SYSTEM

BACKGROUND

Technical Field

The disclosure relates to a control for a neurological disease, and in particular to a method for generating stimulation parameters, an electrical stimulation control apparatus and an electrical stimulation system.

Description of Related Art

Epilepsy is the most common syndrome among the chronic neurological diseases. Approximately 60 million people worldwide suffer from epilepsy, and nearly 30% of them are still unable to effectively control seizures with the current anti-epileptic drugs and require non-drug adjuvant therapy. Although epilepsy surgery is effective, there are still patients who are not suitable for treatment by brain resection and can only choose neuromodulation therapy to reduce occurrences of severe seizures. Both the conventional epilepsy surgery and the new neuromodulation therapy require accurate analysis and judgement of the brainwaves during a seizure to determine the brain region of the seizure or to let an implanter of the neuromodulation therapy determine onset of the seizure.

The duration of an epileptic seizure can be roughly divided into the following phases according to pathophysiological characteristics and features of the brainwave signals, including inter-ictal, pre-ictal, irregular phase, and bursting phase. The latter three stages belong to the ictal phase of the epileptic seizure. Recent studies have indicated that outputting a corresponding electrical stimulus signal during a particular phase has great influence on the effect of neuromodulation. However, the most recent studies have indicated that the stimulation is not equally effective when provided during other phases of the seizure. An electrical stimulation that lasts a long period of time will increase tolerance in the patient, therefore gradually decreasing the effectiveness of the electrical stimulation on the patient. Moreover, the electrical stimulation is very energy intensive. Therefore, how to give a corresponding electrical stimulation after detecting the epileptic seizure and determining the particular phase remains a huge issue for the artificial intelligence neural stimulator.

SUMMARY

This disclosure provides a method for generating stimulation parameters, an electrical stimulation control apparatus, and an electrical stimulation system, which is able to generate corresponding stimulation parameters according to a received brainwave signal.

The method for generating the stimulation parameters of the disclosure includes the following steps. A brainwave signal is sensed. The brainwave signal is decomposed to obtain a first sub-signal and a second sub-signal, in which a frequency of the first sub-signal is higher than a frequency of the second sub-signal. The first sub-signal is analyzed to obtain an intrinsic frequency series, in which the intrinsic frequency series includes at least one frequency component. The second sub-signal is converted to a Boolean signal. The intrinsic frequency series and the Boolean signal, which serve as a set of stimulation parameters, are outputted to the stimulator, enabling the stimulator to generate a stimulus signal.

In an embodiment of the disclosure, the step of decomposing the brainwave signal to obtain the first sub-signal and the second sub-signal includes using an empirical mode decomposition (EMD) algorithm to decompose the brainwave signal into the first sub-signal and the second sub-signal.

In an embodiment of the disclosure, the step of analyzing the first sub-signal to obtain the intrinsic frequency series includes executing a spectrum analysis algorithm on the first sub-signal to obtain the intrinsic frequency series, in which the spectrum analysis algorithm is one of a Fourier transform algorithm, a Wavelet transform algorithm, a normalized direct quadrature algorithm and a normalized Hilbert transform algorithm.

In an embodiment of the disclosure, the step of converting the second sub-signal to the Boolean signal includes executing a binarization algorithm on the second sub-signal to obtain the Boolean signal.

In an embodiment of the disclosure, the execution of the binarization algorithm includes calculating a dominant frequency of the second sub-signal and generating the Boolean signal based on the dominant frequency.

In an embodiment of the disclosure, the method for generating the stimulation parameters further includes receiving the brainwave signal and a serial number corresponding to the brainwave signal, and recording the serial number in a specific series of a parameters table. The intrinsic frequency series and a frequency of the Boolean signal serve as a set of stimulation parameters and are recorded to a position in the parameters table corresponding to the serial number after the intrinsic frequency series and the Boolean signal are obtained.

In an embodiment of the disclosure, after the intrinsic frequency series and the frequency of the Boolean signal serving as the set of stimulation parameters are recorded to the position in the parameters table corresponding to the serial number, the method further includes sequentially inputting the set of stimulation parameters recorded in the parameters table to the stimulator based on the specific series, so as to generate the stimulus signal.

The electrical stimulation control apparatus of the disclosure includes the following components. A signal sensing circuit, which is configured to acquire a brainwave signal. A processor, which is coupled to the signal sensing circuit and configured to decompose the brainwave signal to obtain a first sub-signal and a second sub-signal, in which a frequency of the first sub-signal is higher than a frequency of the second sub-signal. The processor is also configured to analyze the first sub-signal to obtain an intrinsic frequency series, in which the intrinsic frequency series includes at least one frequency component. In addition, the processor is configured to convert the second sub-signal to a Boolean signal. A storage apparatus, which is coupled to the processor and configured to store the intrinsic frequency series and the Boolean signal, in which the processor sends the intrinsic frequency series and the Boolean signal to a stimulator, enabling the stimulator to generate a stimulus signal based on the intrinsic frequency series and the Boolean signal.

The electrical stimulation system of the disclosure includes the following components. A signal sensing circuit, which is configured to receive a brainwave signal. A processor, which is coupled to the signal sensing circuit and configured to decompose the brainwave signal to obtain a first sub-signal and a second sub-signal, in which a frequency of the first sub-signal is higher than a frequency of the second sub-signal. The processor is also configured to analyze the first sub-signal to obtain an intrinsic frequency series, in which the intrinsic frequency series includes at least one frequency component. In addition, the processor is configured to convert the second sub-signal to a Boolean signal. A storage apparatus, which is coupled to the processor and configured to store the intrinsic frequency series and the Boolean signal. A stimulator, which is coupled to the processor and configured to receive the intrinsic frequency series and the Boolean signal, and generate a stimulus signal based on the intrinsic frequency series and the Boolean signal.

Based on the above, the disclosure can generate the corresponding stimulation parameters according to the intrinsic frequency of the brainwave signal.

To make the above-mentioned features and advantages more comprehensible, several embodiments accompanied by drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
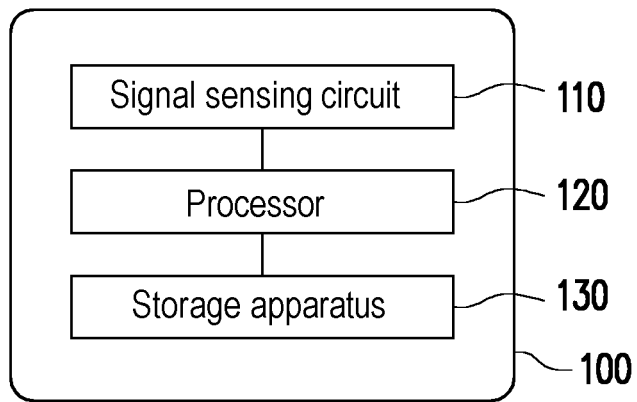
FIG. 1 is a block diagram of an electrical stimulation control apparatus according to an embodiment of the disclosure.

FIG. 1 is a block diagram of an electrical stimulation control apparatus according to an embodiment of the disclosure. With reference to FIG. 1, an electrical stimulation control apparatus 100 includes at least a signal sensing circuit 110, a processor 120 and a storage apparatus 130. The processor 120 is coupled to the signal sensing circuit 110 and the storage apparatus 130. The electrical stimulation control apparatus 100 may be an apparatus with computing capabilities such as a desktop computer, a notebook computer, or a smart phone.

The signal sensing circuit 110 may be an integrated circuit or a microchip. Here, a brainwave signal received by the signal sensing circuit 110 may be a signal of a particular phase, for example, a signal of a bursting phase. Here, for example, a cranial nerve signal in the brainwave signal at a particular phase (such as the bursting phase) during duration of an epileptic seizure may be identified through a detector (not shown), and the cranial nerve signal is subsequently sent to the electrical stimulation control apparatus 100.

In general, calculation steps of a brainwave signal processing algorithm mainly include feature extraction and classification. After spike detection is performed, an interpretation of the epileptic seizure is converted according to its detection result. Acquired features are then inputted into a judgment model for classification judgment. The judgment model generally needs to be trained and built before it can be used, which is realized by methods such as an artificial neural network (ANN), a support vector machine (SVM), a linear classification model, a fuzzy logic model, or an AutoLearn system.

The processor 120 is, for example, a central processing unit (CPU), a physics processing unit (PPU), a programmable microprocessor, an embedded control chip, a digital signal processor (DSP), an application-specific integrated circuit (ASIC), or other similar apparatuses.

The storage apparatus 130 is, for example, any type of fixed or removable random access memory (RAM), a read-only memory (ROM), a flash memory, a hard disk, or other similar apparatuses, or a combination of these apparatuses. Multiple program code snippets are stored in the storage apparatus 130, and the code snippets are executed by the processor 120 after being installed, so as to implement a method for generating stimulation parameters as described in the following.

Figure 2:
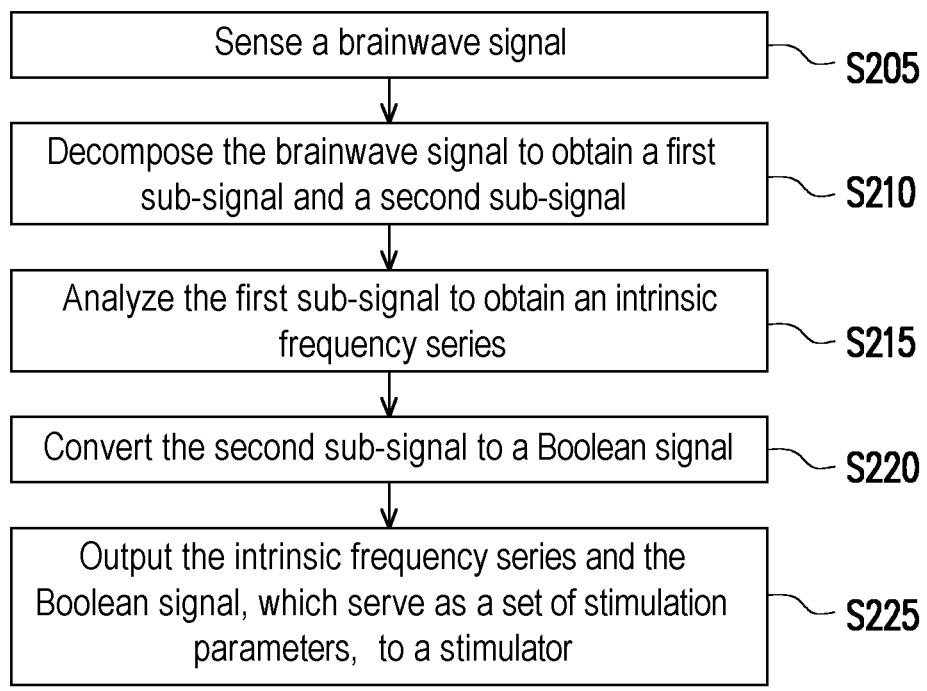
FIG. 2 is a flowchart of a method for generating a stimulus signal according to an embodiment of the disclosure.

FIG. 2 is a flowchart of a method for generating stimulation parameters according to an embodiment of the disclosure. With reference to FIGS. 1 and 2, in step S205, the signal sensing circuit 110 senses the brainwave signal. Next, in step S210, the processor 120 decomposes the brainwave signal to obtain a first sub-signal and a second sub-signal. Here, a frequency of the first sub-signal is higher than a frequency of the second sub-signal. For example, an empirical mode decomposition (EMD) algorithm may be used to decompose the brainwave signal into the first sub-signal and the second sub-signal. The first sub-signal is, for example, a dominant frequency signal.

Subsequently, in step S215, the processor 120 analyzes the first sub-signal to obtain an intrinsic frequency series. The intrinsic frequency series includes at least one frequency component. In addition, in step S220, the processor 120 converts the second sub-signal to a Boolean signal. Here, a binarization algorithm is executed on the second sub-signal to obtain the Boolean signal, and then the Boolean signal serves as a switch signal.

In step S225, the processor 120 outputs the intrinsic frequency series and the Boolean signal, which serve as a set of stimulation parameters, to a stimulator, enabling the stimulator to generate a stimulus signal. For example, after obtaining the intrinsic frequency series and the Boolean signal, the processor 120 records the intrinsic frequency series and a frequency of the Boolean signal, which serve as the set of stimulation parameters, in a parameters table of the storage apparatus 130. Subsequently, the stimulation parameters are sequentially outputted from the parameters table to the stimulator.

Figure 3:
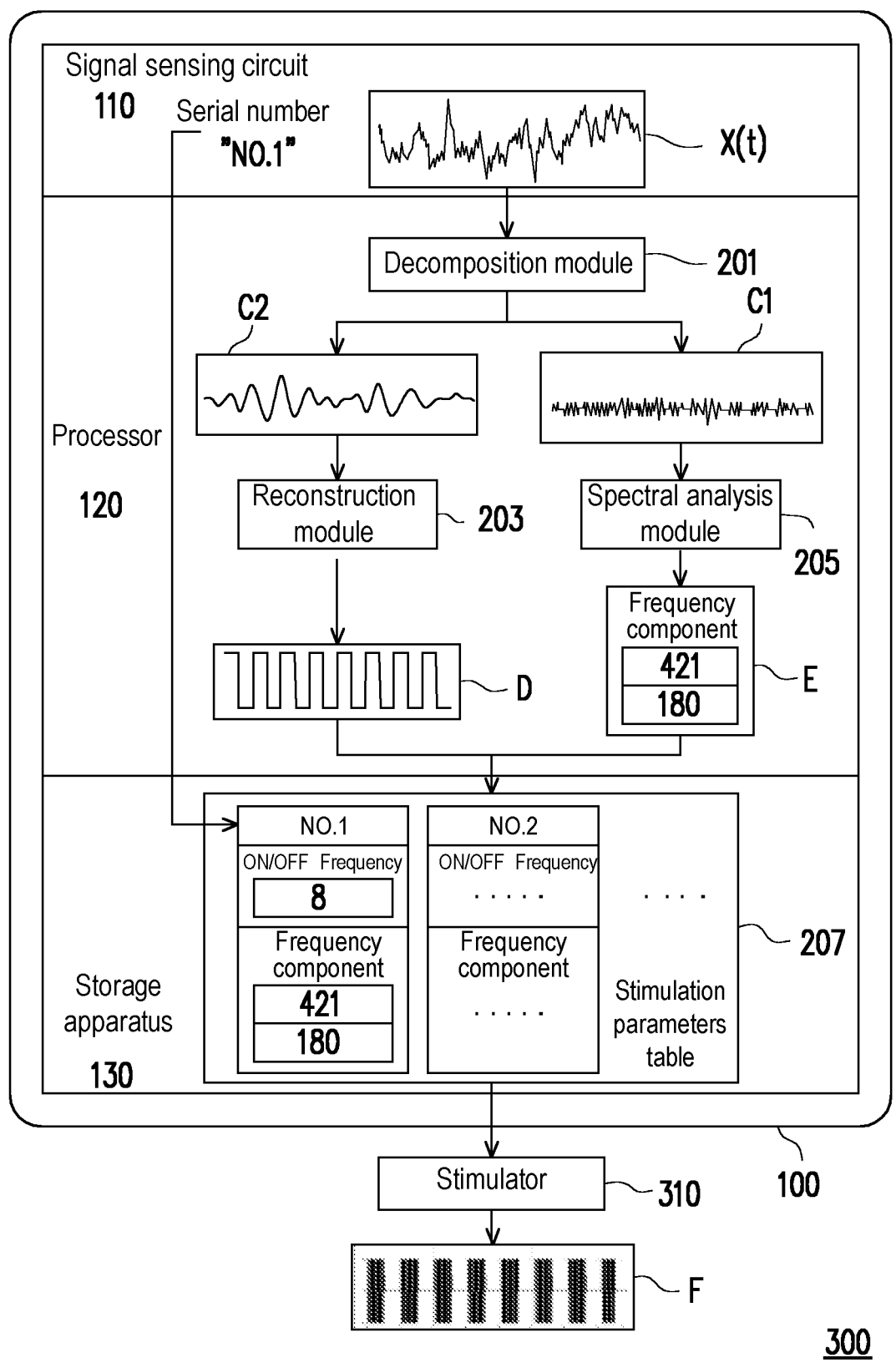
FIG. 3 is a block diagram of an electrical stimulation system according to an embodiment of the disclosure.

The following is an example to illustrate an electrical stimulation system. FIG. 3 is a block diagram of an electrical stimulation system according to an embodiment of the disclosure. With reference to FIG. 3, an electrical stimulation system 300 includes the electrical stimulation control apparatus 100 and a stimulator 310. In the electrical stimulation control apparatus 100 of the embodiment, a decomposition module 201, a reconstruction module 203, and a spectral analysis module 205 are included. The decomposition module 201, the reconstruction module 203 and the spectral analysis module 205 are executed by the processor 120 to obtain stimulation parameters from a brainwave signal X(t). Here, the decomposition module 201 and the spectral analysis module 205 may generate corresponding electrical stimulation parameters for an intrinsic frequency of the brainwave signal X(t) through calculations, while the reconstruction module 203 may adjust the stimulus on and off according to a state of the particular phase. That is, the reconstruction module 203 serves as an activation apparatus for stimulation control.

The signal sensing circuit 110 receives the brainwave signal X(t) and a serial number "NO. 1" corresponding to the brainwave signal X(t). The signal sensing circuit 110 sends the brainwave signal X(t) to the decomposition module 201, and records the serial number "NO. 1" in a specific series of a stimulation parameters table 207.

After receiving the brainwave signal X(t), the decomposition module 201 performs a non-steady state decomposition of the brainwave signal X(t) to obtain a first sub-signal C1 and a second sub-signal C2. The first sub-signal C1 is sent to the spectral analysis module 205 and the second sub-signal C2 is sent to the reconstruction module 203. The spectral analysis module 205 executes a spectrum analysis algorithm on the first sub-signal C1 to obtain an intrinsic frequency series E. The spectrum analysis algorithm is one of a Fourier transform algorithm, a Wavelet transform algorithm, a normalized direct quadrature algorithm and a normalized Hilbert transform algorithm. The intrinsic frequency series E includes at least one frequency component. In the embodiment, the intrinsic frequency series E includes two frequency components, namely 421 Hz and 180 Hz. Subsequently, the two frequency components included in the intrinsic frequency series E are outputted to a position in the stimulation parameters table 207 corresponding to the sequence number "NO. 1".

The reconstruction module 203 performs a binarization algorithm on the second sub-signal C2 to obtain a Boolean signal D. For example, the reconstruction module 203 calculates a dominant frequency of the second sub-signal C2, and then generates the Boolean signal D based on the dominant frequency. The foregoing description is only an example, and is not limited thereto as any binarization algorithm that can convert the second sub-signal C2 to the Boolean signal D may be used. Here, the Boolean signal D serves as a switch signal. Assuming that the dominant frequency of the second sub-signal C2 is 8 Hz, then the Boolean signal D with 8 cycles per second is generated, and each cycle includes two Boolean values (true and false). Here, the reconstruction module 203 serves as the activation apparatus for stimulation control, and the Boolean signal, which serves as the switch signal, is generated through the reconstruction module 203. Subsequently, a frequency (serving as the ON/OFF (switch) frequency, 8 Hz) of the Boolean signal D is outputted to the position corresponding to the serial number "NO. 1" in the stimulation parameters table 207.

In addition, the signal sensing circuit 110 may continue to receive another brainwave signal and a serial number "NO. 2" corresponding to the another brainwave signal. The signal sensing circuit 110 performs the same processing on the brainwave signal with the serial number "NO. 2" as for the brainwave signal X(t) with the serial number "NO. 1", and outputs stimulation parameters (an ON/OFF frequency and frequency components) corresponding to the serial number "NO. 2" to a position corresponding to the serial number "NO. 2" in the stimulation parameter table 207, and so on. Multiple sets of stimulation parameters may be recorded in the stimulation parameters table 207 according to the specific series.

Subsequently, the processor 120 sequentially outputs the corresponding set of stimulation parameters to the stimulator 310 based on the serial numbers recorded in the specific series, enabling the stimulator 310 to generate a stimulus signal F based on the stimulation parameters. That is, the stimulation parameters corresponding to the serial number "NO. 1" are first outputted to the stimulator 310 to generate the stimulus signal F, and then the stimulation parameters corresponding to the serial number "NO. 2" are outputted to the stimulator 310 to generate another stimulus signal, and so on, until the stimulation parameters corresponding to the last serial number in the specific series of the stimulation parameters table 207 are outputted to the stimulator 310 to generate a stimulus signal.

In summary, the disclosure can generate the stimulation parameters corresponding to the brainwave signal, which help to generate the stimulus signals which are more accurate, thereby reducing uncertainty.

Although the disclosure has been disclosed with the foregoing exemplary embodiments, it is not intended to limit the disclosure. Any person skilled in the art can make various changes and modifications within the spirit and scope of the disclosure. Accordingly, the scope of the disclosure is defined by the claims appended hereto and their equivalents.

What is claimed is:
1. A method for generating stimulation parameters, comprising:
   sensing a brainwave signal;
   decomposing the brainwave signal to obtain a first sub-signal and a second sub-signal, wherein a frequency of the first sub-signal is higher than a frequency of the second sub-signal;
   analyzing the first sub-signal to obtain an intrinsic frequency series, wherein the intrinsic frequency series comprises at least one frequency component;
   generating a Boolean signal based on a dominant frequency of the second sub-signal, and serving the Boolean signal as a switch signal, wherein a number of cycle per second of the Boolean signal corresponds to the dominant frequency of the second sub-signal; and
   outputting the intrinsic frequency series and the Boolean signal, which serve as a set of stimulation parameters, to a stimulator, enabling the stimulator to generate a stimulus signal.

2. The method for generating the stimulation parameters according to claim 1, wherein step of decomposing the brainwave signal to obtain the first sub-signal and the second sub-signal comprises:
   using an empirical mode decomposition algorithm to decompose the brainwave signal into the first sub-signal and the second sub-signal.

3. The method for generating the stimulation parameters according to claim 1, wherein step of analyzing the first sub-signal to obtain the intrinsic frequency series comprises:
   executing a spectrum analysis algorithm on the first sub-signal to obtain the intrinsic frequency series,
   wherein the spectrum analysis algorithm is one of a Fourier transform algorithm, a Wavelet transform algorithm, a normalized direct quadrature algorithm, and a normalized Hilbert transform algorithm.

4. The method for generating the stimulation parameters according to claim 1, wherein step of converting the second sub-signal to the Boolean signal comprises:
   executing a binarization algorithm on the second sub-signal to obtain the Boolean signal.

5. The method for generating the stimulation parameters according to claim 4, wherein execution of the binarization algorithm comprises:
   calculating the dominant frequency of the second sub-signal.

6. The method for generating the stimulation parameters according to claim 1, further comprising:
receiving the brainwave signal and a serial number corresponding to the brainwave signal, and recording the serial number in a specific series of a parameters table,
wherein after obtaining the intrinsic frequency series and the Boolean signal, the method further comprises:
recording the intrinsic frequency series and a frequency of the Boolean signal, which serves as the set of stimulation parameters, to a position in the parameters table corresponding to the serial number.

7. The method for generating the stimulation parameters according to claim 6, wherein after the intrinsic frequency series and the frequency of the Boolean signal serving as the set of stimulation parameters are recorded to the position in the parameters table corresponding to the serial number, the method further comprising:
sequentially inputting the set of stimulation parameters recorded in the parameters table to the stimulator based on the specific series, so as to generate the stimulus signal.

8. An electrical stimulation control apparatus, comprising:
a storage apparatus, configured to store a plurality of program code snippets;
a signal sensing circuit, configured to acquire a brainwave signal;
a processor, coupled to the storage apparatus and the signal sensing circuit, and configured to execute the program code snippets to:
decompose the brainwave signal to obtain a first sub-signal and a second sub-signal, wherein a frequency of the first sub-signal is higher than a frequency of the second sub-signal;
analyze the first sub-signal to obtain an intrinsic frequency series, wherein the intrinsic frequency series comprises at least one frequency component; and
generate Boolean signal based on a dominant frequency of the second sub-signal, and serve the Boolean signal as a switch signal,
wherein a number of cycle per second of the Boolean signal corresponds to the dominant frequency of the second sub-signal;
wherein the storage apparatus is configured to store the intrinsic frequency series and the Boolean signal, wherein the processor sends the intrinsic frequency series and the Boolean signal to a stimulator, enabling the stimulator to generate a stimulus signal based on the intrinsic frequency series and the Boolean signal.

9. The electrical stimulation control apparatus according to claim 8, wherein the program code snippets comprise a decomposition module, and the processor is configured to:
execute the decomposition module, and use an empirical mode decomposition algorithm to decompose the brainwave signal into the first sub-signal and the second sub-signal.

10. The electrical stimulation control apparatus according to claim 8, wherein the program code snippets comprise a spectral analysis module, and the processor is configured to:
execute the spectral analysis module to execute a spectrum analysis algorithm on the first sub-signal to obtain the intrinsic frequency series,
wherein the spectrum analysis algorithm is one of a Fourier transform algorithm, a Wavelet transform algorithm, a normalized direct quadrature algorithm, and a normalized Hilbert transform algorithm.

11. The electrical stimulation control apparatus according to claim 8, wherein the program code snippets comprise a reconstruction module, and the processor is configured to:
execute the reconstruction module to execute a binarization algorithm on the second sub-signal to obtain the Boolean signal.

12. The electrical stimulation control apparatus according to claim 11, wherein execution of the binarization algorithm comprises:
calculating the dominant frequency of the second sub-signal.

13. The electrical stimulation control apparatus according to claim 8, wherein signal sensing circuit is configured to:
receive a serial number corresponding to the brainwave signal, and recording the serial number in a specific series of a parameters table, wherein the parameters table is stored in the storage apparatus,
wherein the processor is configured to execute the program code snippets to:
record the intrinsic frequency series and a frequency of the Boolean signal, which serve as a set of stimulation parameters, to a position in the parameters table corresponding to the serial number after the intrinsic frequency series and the Boolean signal are obtained.

14. The electrical stimulation control apparatus according to claim 13, wherein the processor is configured to execute the program code snippets to:
sequentially input the set of stimulation parameters recorded in the parameters table to the stimulator based on the specific series, so as to generate the stimulus signal.

15. An electrical stimulation system, comprising:
a storage apparatus, configured to store a plurality of program code snippets;
a signal sensing circuit, configured to sense a brainwave signal;
a processor, coupled to the storage apparatus and the signal sensing circuit, and configured to execute the program code snippets to:
decompose the brainwave signal to obtain a first sub-signal and a second sub-signal, wherein a frequency of the first sub-signal is higher than a frequency of the second sub-signal;
analyze the first sub-signal to obtain an intrinsic frequency series, wherein the intrinsic frequency series comprises at least one frequency component; and
generate a Boolean signal based on a dominant frequency of the second sub-signal, and serve the Boolean signal as a switch signal, wherein a number of cycle per second of the Boolean signal corresponds to the dominant frequency of the second sub-signal, and the intrinsic frequency series and the Boolean signal are stored in the storage apparatus; and
a stimulator, coupled to the processor, and configured to:
receive the intrinsic frequency series; and
generate a stimulus signal based on the intrinsic frequency series and the Boolean signal.

* * * * *